US012115207B2

(12) United States Patent
Gudkov et al.

(10) Patent No.: US 12,115,207 B2
(45) Date of Patent: Oct. 15, 2024

(54) TREATMENT OF INFLAMMATION

(71) Applicants: Ariel Scientific Innovations Ltd., Ariel (IL); Health Research, Inc., Buffalo, NY (US)

(72) Inventors: Andrei Gudkov, East Aurora, NY (US); Elimelech Nesher, Eli (IL); Albert Pinhasov, Etz Ephraim (IL); Igor Koman, Tel Aviv (IL); Yekaterina Leonova, Buffalo, NY (US)

(73) Assignees: Ariel Scientific Innovations Ltd., Ariel (IL); Health Research, Inc., Buffalo, NY (US)

( * ) Notice: Subject to any disclaimer, the term of this patent is extended or adjusted under 35 U.S.C. 154(b) by 0 days.

(21) Appl. No.: 17/068,849

(22) Filed: Oct. 13, 2020

(65) Prior Publication Data

US 2021/0023164 A1 Jan. 28, 2021

Related U.S. Application Data

(63) Continuation of application No. PCT/IL2019/050417, filed on Apr. 12, 2019.

(51) Int. Cl.
*A61K 38/12* (2006.01)
*A61K 38/08* (2019.01)
*A61P 29/00* (2006.01)

(52) U.S. Cl.
CPC .............. *A61K 38/12* (2013.01); *A61K 38/08* (2013.01); *A61P 29/00* (2018.01)

(58) Field of Classification Search
None
See application file for complete search history.

(56) References Cited

U.S. PATENT DOCUMENTS

| | | | |
|---|---|---|---|
| 5,767,071 A | 6/1998 | Palladino et al. | |
| 7,192,754 B2 | 3/2007 | Kamimura et al. | |
| 7,332,310 B2 | 2/2008 | Nakagawa et al. | |
| 10,266,567 B2* | 4/2019 | Pinhasov | C07K 7/06 |
| 10,906,937 B2* | 2/2021 | Pinhasov | C07K 7/06 |
| 2012/0301968 A1 | 11/2012 | Naito et al. | |
| 2014/0178950 A1 | 6/2014 | Franklin et al. | |
| 2017/0037426 A1 | 2/2017 | Alexandrov et al. | |
| 2018/0072771 A1 | 3/2018 | Pinhasov et al. | |
| 2019/0194253 A1 | 6/2019 | Pinhasov et al. | |

FOREIGN PATENT DOCUMENTS

| | | |
|---|---|---|
| CN | 103044522 | 4/2013 |
| EP | 2345737 | 7/2011 |
| KR | 10-2013-0064710 | 6/2013 |
| WO | WO 2016/139667 | 9/2016 |
| WO | WO 2019/198090 | 10/2019 |

OTHER PUBLICATIONS

Zhong et al. Mimotopes selected with neutralizing antibodies against multiple subtypes of influenza A. Virol J 8, 542 (2011). https://doi.org/10.1186/1743-422X-8-542. https://link.springer.com/article/10.1186/1743-422X-8-542.*
Levi et al. Anti-Cancer Effects of Cyclic Peptide ALOS4 in a Human Melanoma Mouse Model. International Journal of Molecular Sciences. 2021; 22(17):9579. https://doi.org/10.3390/ijms22179579. https://www.mdpi.com/1422-0067/22/17/9579.*
Yacobovich et al. Novel synthetic cyclic integrin avB3 binding peptide ALOS4: Antitumor activity in mouse melanoma models. Oncotarget, 2016, 7.39:63549 (IDS cited).*
Communication Pursuant to Article 94(3) EPC Dated Mar. 9, 2021 From the European Patent Office Re. Application No. 16758561.1. (7 Pages).
EMBL-EBI "Sequence UPI000225E89E: *Streptococcus criceti* HS-6", Database EMBLWGS UniParc [Online], XP055781265, Retrieved From EMBLWGS-EBI, Database Identifier No. EHI74145, 1 P., Nov. 14, 2011.
International Preliminary Report on Patentability Dated Sep. 14, 2017 From the International Bureau of WIPO Re. Application No. PCT/IL2016/050243. (19 Pages).
International Preliminary Report on Patentability Dated Oct. 22, 2020 From the International Bureau of WIPO Re. Application No. PCT/IL2019/050417. (9 Pages).
International Search Report and the Written Opinion Dated Jul. 16, 2019 From the International Searching Authority Re. Application No. PCT/IL2019/050417. (13 Pages).
International Search Report and the Written Opinion Dated May 19, 2016 From the International Searching Authority Re. Application No. PCT/IL2016/050243.
Notice of Allowance Dated Dec. 5, 2018 From the US Patent and Trademark Office Re. U.S. Appl. No. 15/554,719. (7 pages).
Notice of Allowance Dated Oct. 15, 2020 from the US Patent and Trademark Office Re. U.S. Appl. No. 16/299,206. (3 pages).
Official Action Dated Aug. 13, 2020 from the US Patent and Trademark Office Re. U.S. Appl. No. 16/299,206. (11 pages).
Official Action Dated Jul. 19, 2018 From the US Patent and Trademark Office Re. U.S. Appl. No. 15/554,719. (17 pages).
Official Action Dated Mar. 26, 2020 from the US Patent and Trademark Office Re. U.S. Appl. No. 16/299,206. (21 pages).
Supplementary European Search Report and the European Search Opinion Dated Feb. 8, 2019 From the European Patent Office Re. Application No. 16758561.1. (15 Pages).
Supplementary Partial European Search Report and the European Provisional Opinion [Communication Pursuant to Rule 164(1) EPC] Dated Nov. 6, 2018 From the European Patent Office Re. Application No. 16758561.1. (19 Pages).
Benveniste et al. "Type I Interferons as Anti-Inflammatory Mediators", Science's STKE, 2007(416): pe70-1-pe70-4, Dec. 11, 2007.
Capasso et al. "RGDechi-hCit: AlphavBeta3 Selective Pro-Apoptotic Peptide as Potential Carrier for Drug Delivery Into Melanoma Metastatic Cells", PLOS ONE, 9(9): e106441-1-e106441-10, Sep. 23, 2014. Figs.5, 7-8.

(Continued)

*Primary Examiner* — Maury A Audet

(57) ABSTRACT

A method of treating an inflammatory disease or disorder is disclosed. The method comprises administering to the subject a therapeutically effective amount of a peptide comprising an amino acid sequence selected from the group consisting of SEQ ID NOs: 11-15. The inflammatory disease is not cancer, osteoporosis, rheumatic arthritis, osteoarthritis or angiogenesis-related eye disease.

1 Claim, 6 Drawing Sheets

Figure 1A:
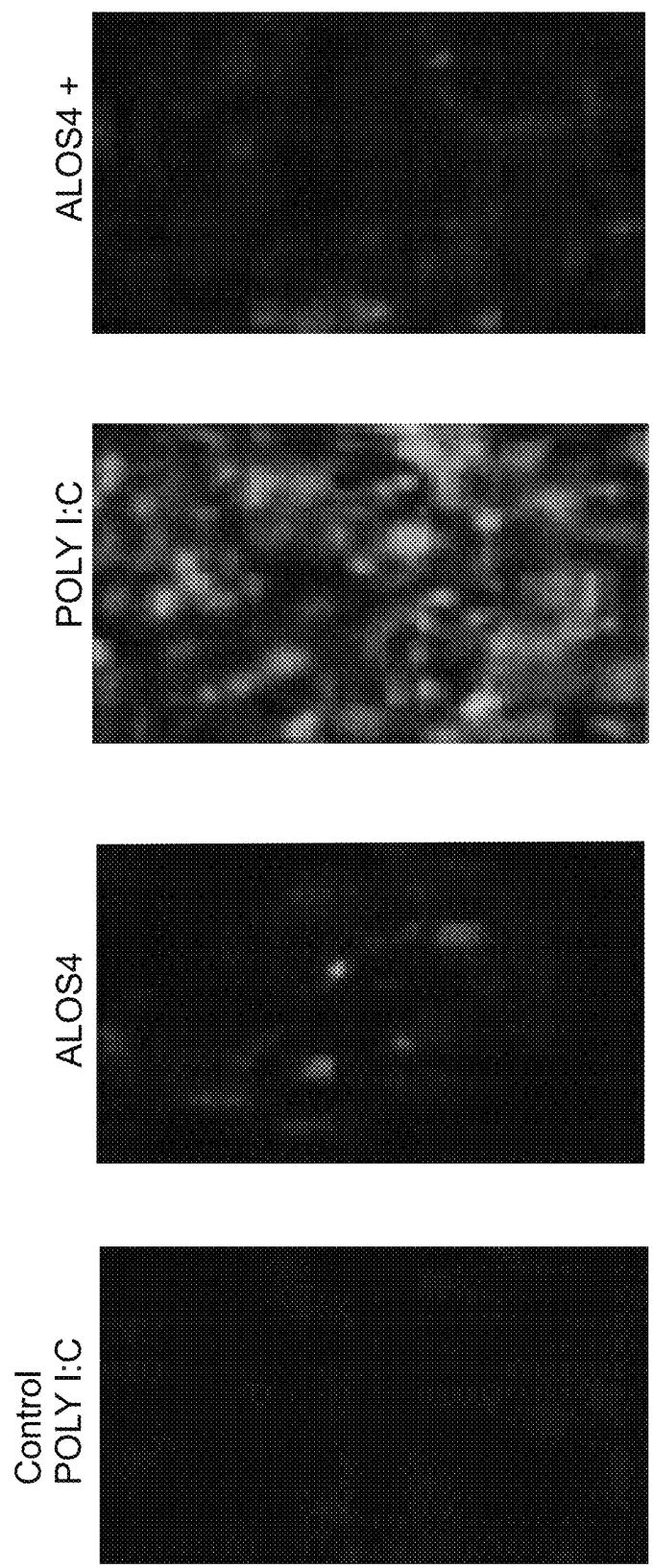

Specification includes a Sequence Listing.

(56) References Cited

OTHER PUBLICATIONS

Cazorla et al. "Cyclotraxin-B, the First Highly Potent and Selective TrkB Inhibitor, Has Anxiolytic Properties in Mice", PLoS ONE, XP055517106, 5(3): e9777-1-e9777-17, Published Online Mar. 19, 2010.
Cohen et al. "Abstract 17: Non-RGD-Based Strategies to Target the Thyroid Hormone Receptor-Integrin AvBeta3: Lessons From Myeloma Cells.", Abstracts of AACR Special Conference on Hematologic Malignancies: Translating Discoveries to Novel Therapies, Philadelphia, PA, USA, Sep. 20-23, 2014, Clinical Cancer Research, XP055515925, 21(17 Suppl.): # A17, Sep. 2015.
Francis "Selective Peptide to AlphavBeta3 Integrin for the Treatment of Melanoma", Ariel University R&D Company Ltd., Liefe Sciences and Biotechnology, p. 1-9, Dec. 28, 2014.
Franklin et al. "Sec ID No. 16042, Sequence Detail(s) for U.S. Appl. No. 14/099,704", 2 Pages, Jun. 26, 2014.
Liu et al. "Type I Interferons Promote the Survival and Proinflammatory Properties of Transitional B Cells in Systemic Lupus Erythematosus Patients", Cellular & Molecular Immunology, p. 1-13, Published Online Mar. 21, 2018.
Matsuda et al. "Brain-Derived Neurotrophic Factor Induces Migration of Endothelial Cells Through a TrkB-ERK-Integrin AlphavBeta3-FAK Cascade", Journal of Cellular Physiology, XP055517252, 227(5): 2123-2129, Published Online Jul. 18, 2011.
Nakagawa et al. "Seq ID No. 5036, Sequence Detail(s) for U.S. Appl. No. 10/805,394", 1 Page, Feb. 19, 2008.
Ngubane et al. "High-Throughput Sequencing Enhanced Phage Display Identifies Peptides That Bind Myobacteria", PLOS ONE, 8(11): e77844-1-e77844-11, Nov. 12, 2013. Table 1.
Redko et al. "Toward the Development of a Novel Non-RGD Cyclic Peptide Drug Conjugate for Treatment of Human Metastatic Melanoma", Oncotarget, XP055515798, 8(1): 757-768, Published Online Oct. 19, 2016.
Rodgers et al. "Integrin AvBeta3 Binds a Unique Non-RGD Site Near the C-Terminus of Human Tropoelastin", Biochimie, XP055515938, 86(3): 173-178, Available Online Apr. 2, 2004.
Thannhauser et al. "Determination of the Cysteine and Cystine Content of Proteins by Amino Acid Analysis: Application to the Characterization of Disulfide-Coupled Folding Intermediates", Journal of Protein Chemistry, 17(1): 37-43, 1998.
Whyte et al. "Serotonin Transporter and Integrin Beta 3 Genes Interact to Modulate Serotonin Uptake in Mouse Brain", Neurochemistry International, 73: 122-126, Available Online Sep. 29, 2013.
Yakobovich et al. "Novel Synthetic Cyclic Integrin AvBeta3 Binding Peptide ALOS4: Antitumor Activity in Mouse Melanoma Models", Oncotarget, XP055515801, 7(39): 63549-63560, Published Online Aug. 18, 2016.
Zhong et al. "Mimotopes Selected With Neutralizing Antibodies Against Multiple Subtypes of Influenza A", Virology Journal, 8(542): 1-11, Dec. 15, 2011.
Supplementary European Search Report and the European Search Opinion Dated Jan. 4, 2022 From the European Patent Office Re. Application No. 19784555.5. (8 Pages).
Roveri et al. "Peptides for Tumor-Specific Drug Targeting: State of the Art and Beyond", Journal of Materials Chemistry B, 5:4318-41364, Feb. 27, 2017.
Fischbach et al. "Annotation of Streptomyces Pristinaespiralis ATCC 15486", Database NCBI UNIProt/KB [Online], XP055781265, Retrieved vom EMBLWGS: B5H7G1_ STRPR, Database Accession No. B5H7G1, 1 P., Oct. 14, 2008.
Communication Pursuant to Article 94(3) EPC Dated Apr. 11, 2024 From the European Patent Office Re. Application No. 19784555.5 (6 Pages).

* cited by examiner

TREATMENT OF INFLAMMATION

RELATED APPLICATIONS

This application is a Continuation of PCT Patent Application No. PCT/IL2019/050417 having International filing date of Apr. 12, 2019, which claims the benefit of priority under 35 USC § 119(e) of U.S. Provisional Patent Application No. 62/657,035 filed on Apr. 13, 2018. The contents of the above applications are all incorporated by reference as if fully set forth herein in their entirety.

SEQUENCE LISTING STATEMENT

The ASCII file, entitled 84820SequenceListing.txt, created on Oct. 13, 2020, comprising 4,312 bytes, submitted concurrently with the filing of this application is incorporated herein by reference.

FIELD AND BACKGROUND OF THE INVENTION

The present invention, in some embodiments thereof, relates to peptide agents for the treatment of inflammation.

Inflammation is a complex of sequential changes expressing the response to damage of cells and vascularized tissues. When tissue injury occurs, whether it is caused by bacteria, trauma, chemicals, heat, or any other phenomenon, the substance histamine, along with other humoral substances, is liberated by the damaged tissue into the surrounding fluids. It is a protective attempt by the organism to remove the injurious stimuli as well as initiating the healing process.

The main features of the inflammatory response are vasodilation, i.e. widening of the blood vessels to increase the blood flow to the infected area; increased vascular permeability which allows diffusible components to enter the site; cellular infiltration by chemotaxis; or the directed movement of inflammatory cells through the walls of blood vessels into the site of injury; changes in biosynthetic, metabolic, and catabolic profiles of many organs; and activation of cells of the immune system as well as of complex enzymatic systems of blood plasma. Inflammation which runs unchecked can, however, lead to a host of diseases, such as hay fever, atherosclerosis and rheumatoid arthritis.

There are two forms of inflammation, commonly referred to as acute inflammation and chronic inflammation. Acute inflammation is the initial response of the body to harmful stimuli and is achieved by the increased movement of plasma and leukocytes from the blood into the injured tissues. Acute inflammation can be divided into several phases. The earliest, gross event of an inflammatory response is temporary vasoconstriction, i. e., narrowing of blood vessels caused by contraction of smooth muscle in the vessel walls which can be seen as blanching (whitening) of the skin. This is followed by several phases that occur minutes, hours and days later. The first is the acute vascular response which follows within seconds of the tissue injury and lasts for several minutes. This results from vasodilation and increased capillary permeability due to alterations in the vascular endothelium which leads to increased blood flow (hyperemia) that causes redness (erythema) and the entry of fluid into the tissues (edema).

The acute vascular response can be followed by an acute cellular response which takes place over the next few hours. The hallmark of this phase is the appearance of granulocytes, particularly neutrophils, in the tissues. These cells first attach themselves to the endothelial cells within the blood vessels (margination) and then cross into the surrounding tissue (diapedesis). During this phase erythrocytes may also leak into the tissues and a hemorrhage can occur. If the vessel is damaged, fibrinogen and fibronectin are deposited at the site of injury, platelets aggregate and become activated, and the red cells stack together in what are called "rouleau" to help stop bleeding and aid clot formation. The dead and dying cells contribute to pus formation. If the damage is sufficiently severe, a chronic cellular response may follow over the next few days. A characteristic of this phase of inflammation is the appearance of a mononuclear cell infiltrate composed of macrophages and lymphocytes. The macrophages are involved in microbial killing, in clearing up cellular and tissue debris, and in remodeling of tissues.

Chronic inflammation is an inflammatory response of prolonged duration—weeks, months or indefinitely—whose extended time course is provoked by persistence of the causative stimulus to inflammation in the tissue. The inflammatory process inevitably causes tissue damage and is accompanied by simultaneous attempts at healing and repair. The exact nature, extent and time course of chronic inflammation is variable depending on a balance between the causative agent and the attempts of the body to remove it.

Etiological agents producing chronic inflammation include:

(i) infectious organisms that can avoid or resist host defenses and so persist in the tissue for a prolonged period, including *Mycobacterium tuberculosis*, Actinomycetes, and numerous fungi, protozoa and metazoal parasites. Such organisms are in general able to avoid phagocytosis or survive within phagocytic cells, and tend not to produce toxins causing acute tissue damage;

(ii) infectious organisms that are not innately resistant but persist in damaged regions where they are protected from host defenses. An example is bacteria which grow in the pus within an un-drained abscess cavity where they are protected both from host immunity and from blood-borne therapeutic agents, e. g. antibiotics. Some locations are particularly prone to chronic abscess formation, e. g. bone and pleural cavities;

(iii) irritant non-living foreign material that cannot be removed by enzymatic breakdown or phagocytosis. Examples include a wide range of materials implanted into wounds (wood splinters, grit, metals and plastics), inhaled (silica dust and other particles or fibers) or deliberately introduced (surgical prostheses, sutures, etc.), including transplants. Dead tissue components that cannot be broken down may have similar effects, e. g. keratin squames from a ruptured epidermoid cyst or fragments of dead bone (sequestrum) in osteomyelitis.

(iv) in some cases the stimulus to chronic inflammation may be a normal tissue component. This occurs in inflammatory diseases where the disease process is initiated and maintained because of an abnormality in the regulation of the body's immune response to its own tissues—the so-called auto-immune diseases. This response is seen in elderly and aging subjects; and (v) for many diseases characterized by a chronic inflammatory pathological process the underlying cause remains unknown. An example is Crohn's disease.

Related art: WO2016/139667.

SUMMARY OF THE INVENTION

According to an aspect of the present invention there is provided a method of treating an inflammatory disease or disorder in a subject in need thereof, the method comprising administering to the subject a therapeutically effective amount of a peptide comprising an amino acid sequence selected from the group consisting of SEQ ID NOs: 11-15, wherein said inflammatory disease is not cancer, osteoporosis, rheumatic arthritis, osteoarthritis or angiogenesis-related eye disease, thereby treating the inflammatory disease of disorder.

According to an aspect of the present invention there is provided a peptide comprising an amino acid sequence selected from the group consisting of SEQ ID NOs: 11-15 for use in treating an inflammatory disease or disorder, with the proviso that the disease is not cancer, osteoporosis, rheumatic arthritis, osteoarthritis or angiogenesis-related eye disease.

According to an embodiment of the present invention, the disease or disorder is atherosclerosis or a graft rejection disease.

According to an embodiment of the present invention, the graft rejection disease is selected from the group consisting of chronic graft rejection, subacute graft rejection, hyperacute graft rejection, acute graft rejection and graft versus host disease.

According to an embodiment of the present invention, the graft rejection disease is graft versus host disease.

According to an embodiment of the present invention, the inflammatory disease or disorder is not associated with a behavioral condition.

According to an embodiment of the present invention, the inflammatory disease or disorder is associated with a type I interferon activity.

According to an embodiment of the present invention, the peptide is cyclic.

According to an embodiment of the present invention, the peptide is capable of binding to αVβ3 integrin.

According to an embodiment of the present invention, the N terminus of the peptide is bound to the C terminus of the peptide.

According to an embodiment of the present invention, the N terminal amino acid and the C terminal amino acids are cysteines.

According to an embodiment of the present invention, the peptide is no more than 20 amino acids in length.

According to an embodiment of the present invention, the peptide is no more than 10 amino acids in length.

According to an embodiment of the present invention, the peptide comprises the sequence selected from the group as set forth in SEQ ID NOs: 1-5.

According to an embodiment of the present invention, the peptide comprises the sequence as set forth in SEQ ID NO: 4.

According to an embodiment of the present invention, the peptide consists of the sequence selected from the group as set forth in SEQ ID NOs: 1-5.

According to an embodiment of the present invention, the peptide consists of the sequence as set forth in SEQ ID NO: 4.

According to an embodiment of the present invention, the peptide consists of the sequence selected from the group as set forth in SEQ ID NOs: 11-15.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1B:
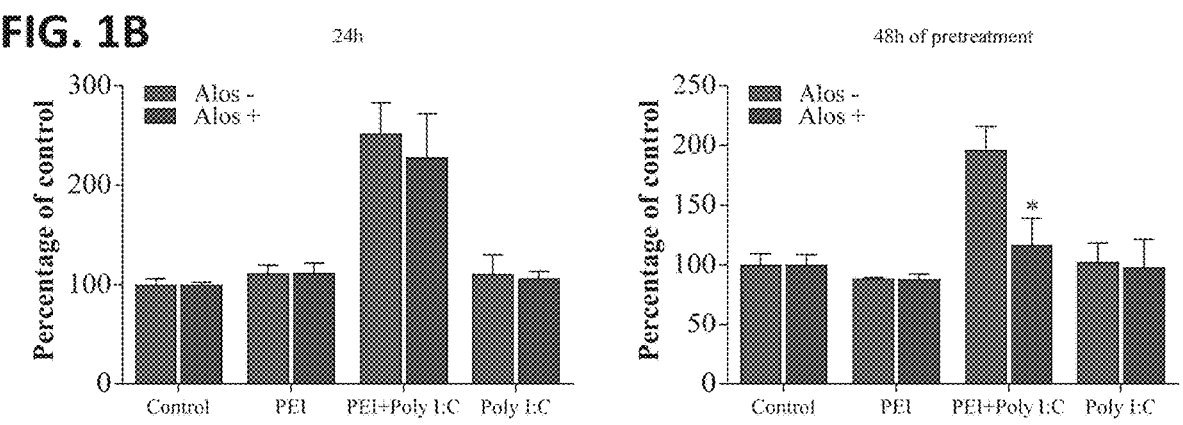
Figure 1C:
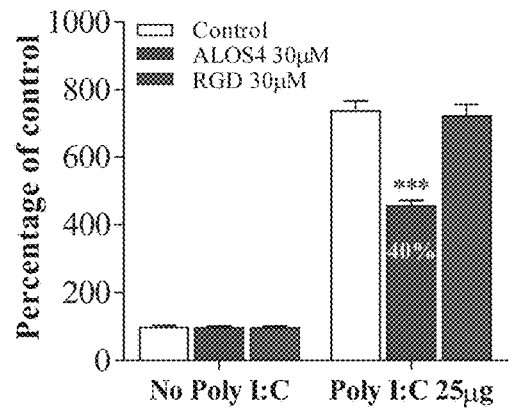

In the drawings:

FIGS. 1A-C. Anti-inflammatory effect of ALOS4. Pretreatment with 0.3 μM of ALOS4 for 48 hours suppressed the ability of treated HT1080 ISRE mCherry cells (A, C) as well as HCT116 ISRE Luc cells (B) to induce interferon type I signaling in response to mimics of double stranded RNA (Poly I:C).

FIGS. 2A-D. Effect of ALOS4 sub-chronic treatment on inflammatory markers expression. Effect of ALOS4 on serum cytokines expression profile: (A) Interleukins, and (B) Jak-STAT signaling pathway. Data shown for submissive mice sub-chronically treated with 10 and 30 mg/kg of ALOS4, as well as with saline for control. Each column represents the pull of serum from 10 mice. (C) H&E staining of fat pad of submissive mice following the treatment with 10 and 30 mg/kg of ALOS4, and saline as a control. Images were acquired using Axio Observer Zeiss 5 Microscope with a 20× objective. The crown-like structures were quantified by manual scoring and significance was assessed using one-way ANOVA with () at $p<0.01$, and (*) at $p<0.001$. (D) Inhibitory effect of ALOS4 on macrophage differentiation induced by LPS. Nitric oxide, used as an indicator of the differentiation macrophages to pro-inflammatory, demonstrated a significant dose-dependent decrease after ALOS4 treatment. Significance was assessed using One-way ANOVA() at $p<0.01$ and (*) at $p<0.001$.

DESCRIPTION OF SPECIFIC EMBODIMENTS OF THE INVENTION

The present invention, in some embodiments thereof, relates to peptide agents for the treatment of inflammatory diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 2A:
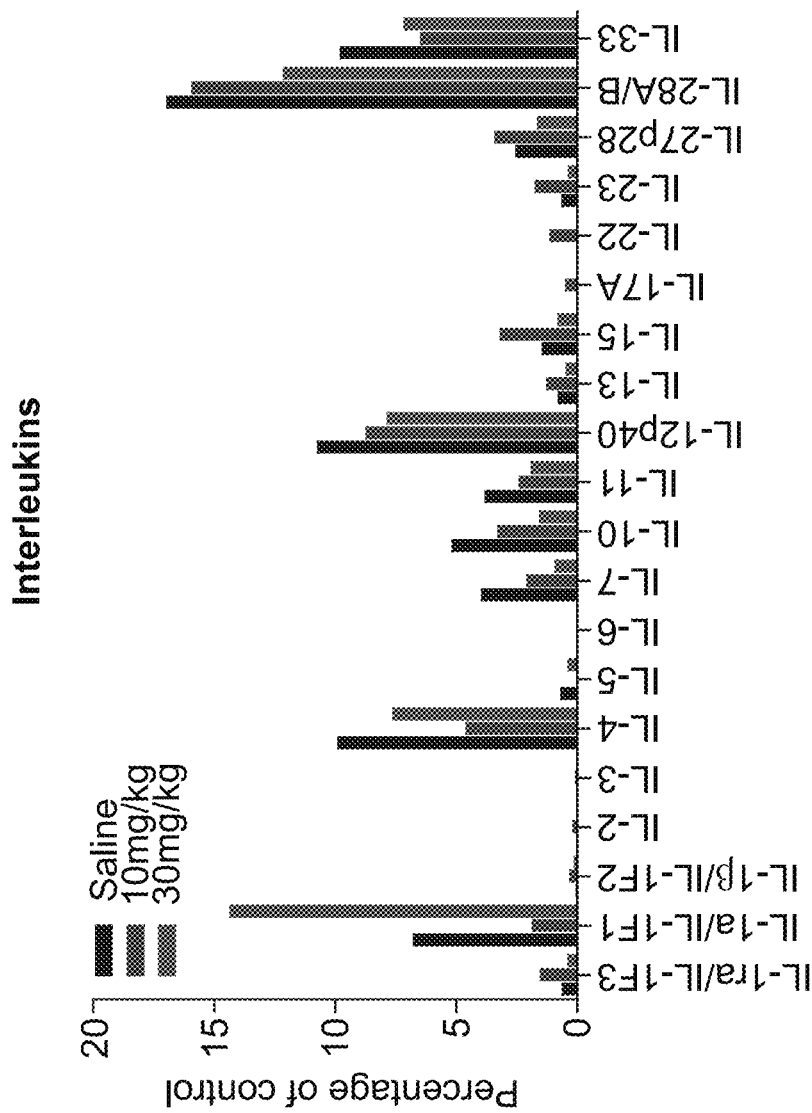
Figure 2B:
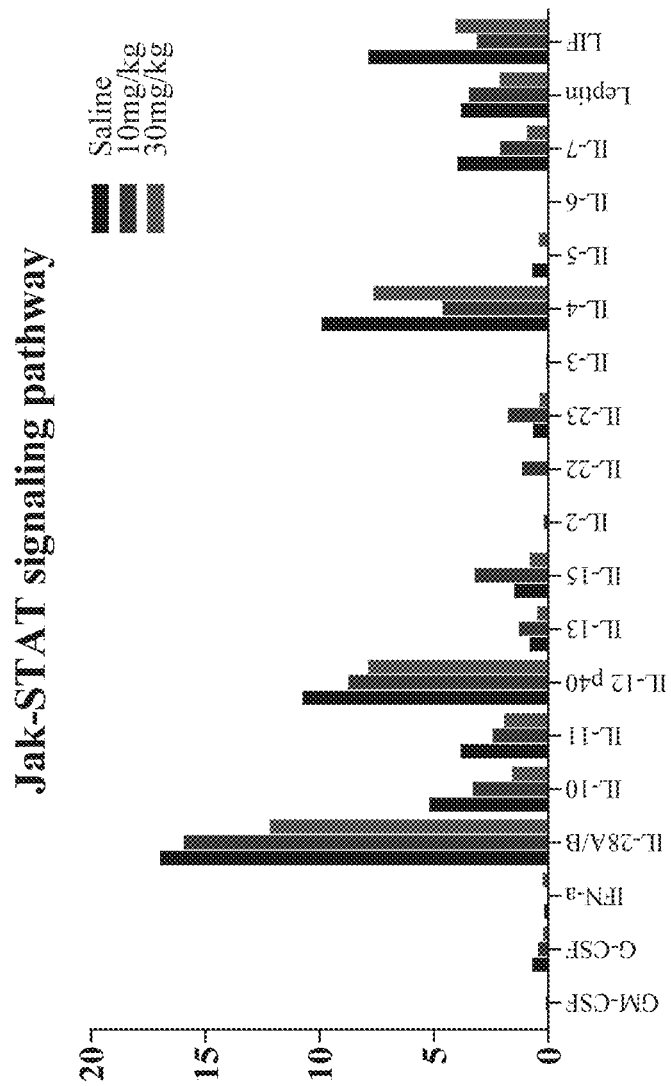
Figure 2C:
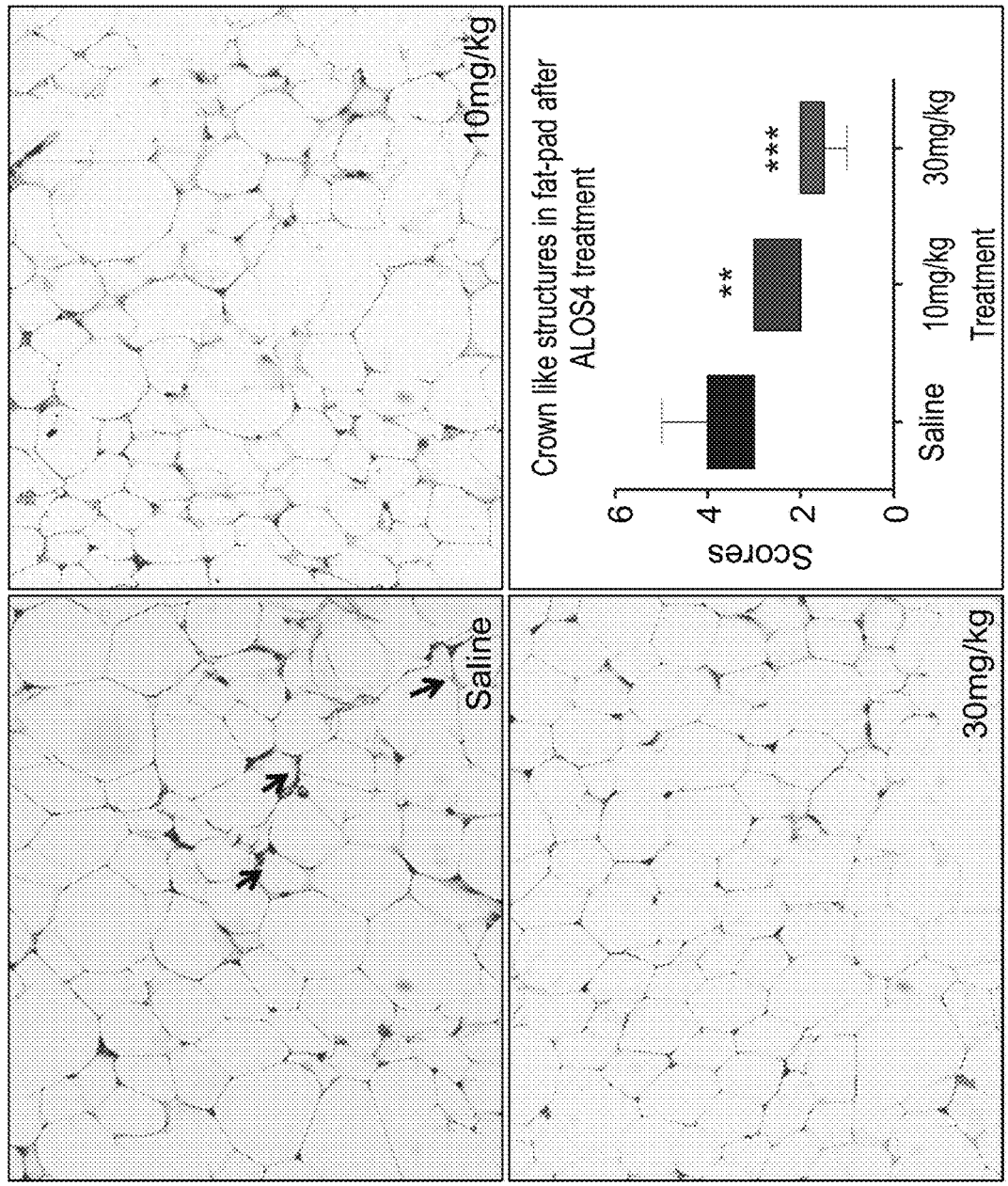

Peptides which bind specifically to the integrin αvβ3 receptor are disclosed in WO2016/139667. The present inventors have now surprisingly found that such peptides show an anti-inflammatory effect. For example, as illustrated in FIGS. 1A-C, the peptide ALOS4 suppressed the ability of treated cells to induce interferon type I signaling in response to mimics of double stranded RNA (Poly I:C). In addition, the present inventors showed that sub-chronic treatment of ALOS4 significantly reduced inflammatory marker expression (FIGS. 2A-C).

Based on these findings, the present inventors conclude that peptide agents that bind to the integrin αvβ3 receptor may be beneficial for the treatment of inflammatory diseases.

Thus, according to an aspect of some embodiments of the present invention there is provided a method of treating an inflammatory disease or disorder in a subject in need thereof, the method comprising administering to the subject a therapeutically effective amount of a peptide comprising an amino acid sequence selected from the group consisting of SEQ ID NOs: 11-15, thereby treating the disease, wherein said inflammatory disease is not cancer, osteoporosis, rheumatic arthritis, osteoarthritis or angiogenesis-related eye disease, thereby treating the inflammatory disease of disorder.

According to some embodiments of the invention, said inflammatory disease is associated with a type I interferon activity.

According to some embodiments of the invention, the peptide is cyclic.

According to some embodiments of the invention, the peptide is capable of binding to αVβ3 integrin.

According to some embodiments of the invention, the N terminus of the peptide is bound to the C terminus of the peptide.

According to some embodiments of the invention, the N terminal amino acid and the C terminal amino acids are cysteines.

According to some embodiments of the invention, the peptide is no more than 20 amino acids in length.

According to some embodiments of the invention, the peptide is no more than 10 amino acids in length.

According to some embodiments of the invention, the peptides comprise the sequence selected from the group as set forth in SEQ ID NOs: 1-5.

According to some embodiments of the invention, the peptides consist of the sequence selected from the group as set forth in SEQ ID NOs: 1-5.

According to some embodiments of the invention, the peptides consist of the sequence selected from the group as set forth in SEQ ID NOs: 11-15.

According to a specific embodiment, the inflammation is associated with type I interferon activity. Hence an effective amount of the peptide will reduce the interferon activity, thereby reducing inflammation.

In particular embodiments the inflammatory disease is not cancer, osteoporosis, rheumatic arthritis, osteoarthritis or an angiogenesis-related eye disease.

According to a particular embodiment, the inflammation is a result of a wound or tissue damage (e.g. due to radiation).

According to a particular embodiment, the inflammation is a result of an irritant or a pathogen (e.g. infection).

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

According to a specific embodiment, the peptide of this aspect of the present invention is used to treat (and/or prevent) atherosclerosis.

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, *Pemphigus vulgaris*, bullous pemphigoid and *Pemphigus foliaceus*.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B.

et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, *Pemphigus vulgaris*, bullous pemphigoid and *Pemphigus foliaceus*.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (*Nobile*-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

As mentioned, in some embodiments, the peptides are capable of binding to αVβ3 integrin. According to one embodiment, the peptides bind in vitro to αVβ3 integrin. According to another embodiment, the peptides bind in vivo to αVβ3 integrin. This protein is a type of integrin that is a receptor for vitronectin. It consists of two components, integrin alpha V (CD51 ref seq NM_002210.4) and integrin beta 3 (CD61, ref seq NM_000212).

The peptides disclosed herein, may be capable of binding other integrins such as αVβ5 integrin and/or α5β1 integrin.

Binding affinity can be measured by any assay known or available to those skilled in the art, including but not limited to BIAcore measurements, ELISA assays, competition assays, etc. Bioactivity can be measured in vivo or in vitro by any assay known or available to those skilled in the art.

According to one embodiment, binding is measured using an antibody which is capable of specifically recognizing the peptides disclosed herein.

According to another embodiment, the binding is measured using peptides which are attached to a detectable moiety, wherein the αVβ3 integrin is immobilized onto a solid support.

Preferably, the peptide binds (e.g. in vitro) to the αVβ3 integrin with a Kd of at least 10 uM-100 nM.

According to another embodiment, the peptides do not bind to the RGD binding site of αVβ3 integrin.

According to still another embodiment, the peptides bind with at least 2 fold, at least 5 fold, at least 10 fold or at least 20 fold higher affinity to αVβ3 than α11bβ3 and/or α5β1 integrin. The peptides described herein may comprise at least one of the following sequences: NLSSSWI (SEQ ID NO: 11), PPSNHLL (SEQ ID NO: 12), APSPSRL (SEQ ID NO: 13), SSAGSLF (SEQ ID NO: 14) or PLHARLP (SEQ ID NO: 15).

According to another embodiment, the peptides of this aspect of the present invention consist of at least one of the following sequences: NLSSSWI (SEQ ID NO: 11), PPSNHLL (SEQ ID NO: 12), APSPSRL (SEQ ID NO: 13), SSAGSLF (SEQ ID NO: 14) or PLHARLP (SEQ ID NO: 15).

The peptides described herein are at least 7 amino acids in length. Longer peptides are also contemplated by the inventors. Thus, the peptides may be 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids or 20 amino acids.

According to one embodiment, the peptides are not longer than 20 amino acids, 30 amino acids, 40 amino acids or 50 amino acids.

According to a particular embodiment the peptides are 9 amino acids, wherein each of the peptide sequences provided herein above are flanked by cysteine residues.

Accordingly, the peptides may comprise any of the following sequences: CNLSSSWIC (SEQ ID NO: 1), CPPSNHLLC (SEQ ID NO: 2), CAPSPSRLC (SEQ ID NO: 3), CSSAGSLFC (SEQ ID NO: 4) or CPLHARLPC (SEQ ID NO: 5).

According to another embodiment, the peptides consist of any of the following sequences: CNLSSSWIC (SEQ ID NO: 1), CPPSNHLLC (SEQ ID NO: 2), CAPSPSRLC (SEQ ID NO: 3), CSSAGSLFC (SEQ ID NO: 4) or CPLHARLPC (SEQ ID NO: 5).

The term "peptide" as used herein refers to a polymer of natural or synthetic amino acids, encompassing native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides even more stable while in a body or more capable of penetrating into cells. The peptide is shorter (e.g. a fragment of) than a naturally-occurring, full length protein.

Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc.).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |

TABLE 2-continued

| Non-conventional amino acid | Code | Non-conventional amino acid | Code |
|---|---|---|---|
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |

TABLE 2-continued

| Non-conventional amino acid | Code | Non-conventional amino acid | Code |
|---|---|---|---|
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval | L-N-methylhomophenylalanine | Nmhphe |
|  | Nnbhm |  |  |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc |  |  |

The present teachings further contemplate cyclic peptides or cyclic structures within the peptides. Methods of cyclization are well known in the art, see for instance in WO2010/041237, which is hereby incorporated by reference.

The cyclization may be via N- to C-terminal, N-terminal to side chain and N-terminal to backbone, C-terminal to side chain, C-terminal to backbone, side chain to backbone and side chain to side chain, as well as backbone to backbone cyclization.

Cyclization of the polypeptide may also take place through non-amino acid organic moieties comprised in the polypeptide.

For example, a peptide according to the teachings of the present invention can include at least two cysteine residues flanking the core peptide sequence (as described herein above). In this case, cyclization can be generated via formation of S—S bonds between the two Cys residues. Side chain to side chain cyclization can also be generated via formation of an interaction bond of the formula —(—CH$_2$-)n-S—CH$_2$—C—, wherein n=1 or 2, which is possible, for example, through incorporation of Cys or homoCys and reaction of its free SH group with, e.g., bromoacetylated Lys, Orn, Dab or Dap. Furthermore, cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH$_2$)n-COOH)—C(R)H—COOH or H—N((CH$_2$)n-COOH)—C(R)H—NH$_2$, wherein n=1-4, and further wherein R is any natural or non-natural side chain of an amino acid.

Cyclic peptides can be joined together by a peptide bond, a disulfide linkage between two amino acid residues such as cysteine residues, or by any other suitable linking group. Nonpeptidal linking groups can be any chemical moiety that can react with functional groups at each end of the peptide chain to form a link therebetween. For example, two ends of a peptide chain can be linked together by a non-protein amino acid such as 3-aminobutyric acid or by a disulfide formed from nonpeptidal thiol groups such as a thioglycolic amide at the amino terminal end and amide formed from 2-aminoethane thiol at the carboxy terminal end, for example.

Hereinthroughout, the phrases "disulfide bridge" and "disulfide bond" are used interchangeably, and describe a —S—S— bond.

The linker may comprise additional amino acids linked together by peptide bonds which serve as spacers such that the linker does not interfere with the biological activity of the final compound. The linker is preferably made up of amino acids linked together by peptide bonds. Thus, in preferred embodiments, the linker is made up of from 1 to 10 amino acids linked by peptide bonds, wherein the amino acids are selected from the 20 naturally occurring amino acids. Some of these amino acids may be glycosylated, as is well understood by those in the art. In a more preferred embodiment, besides cysteine the amino acids in the linker are selected from glycine, alanine, proline, asparagine, glutamine, and lysine. Even more preferably, besides cysteine, the linker is made up of a majority of amino acids that are sterically unhindered, such as glycine and alanine.

Thus, according to one embodiment the linker comprises the sequence cysteine-glycine.

According to another embodiment the cyclization is effected using a coupling agent.

The term "coupling agent", as used herein, refers to a reagent that can catalyze or form a bond between two or more functional groups intra-molecularly, inter-molecularly or both. Coupling agents are widely used to increase polymeric networks and promote crosslinking between polymeric chains, hence, in the context of some embodiments of the present invention, the coupling agent is such that can promote crosslinking between polymeric chains; or such that can promote crosslinking between amino functional groups and carboxylic functional groups, or between other chemically compatible functional groups of polymeric chains. In some embodiments of the present invention the term "coupling agent" may be replaced with the term "crosslinking agent". In some embodiments, one of the polymers serves as the coupling agent and acts as a crosslinking polymer.

By "chemically compatible" it is meant that two or more types of functional groups can react with one another so as to form a bond.

According to some embodiments of the present invention, the coupling agent can be selected according to the type of functional groups and the nature of the crosslinking bond that can be formed therebetween. For example, carboxyl coupling directly to an amine can be afforded using a carbodiimide type coupling agent, such as EDC; amines may be coupled to carboxyls, carbonyls and other reactive functional groups by N-hydroxysuccinimide esters (NHS-esters), imidoester, PFP-ester or hydroxymethyl phosphine; sulfhydryls may be coupled to carboxyls, carbonyls, amines and other reactive functional groups by maleimide, haloacetyl (bromo- or iodo-), pyridyldisulfide and vinyl sulfone; aldehydes as in oxidized carbohydrates, may be coupled to other reactive functional groups with hydrazide; and hydroxyl may be coupled to carboxyls, carbonyls, amines and other reactive functional groups with isocyanate.

Hence, suitable coupling agents that can be used in some embodiments of the present invention include, but are not limited to, carbodiimides, NHS-esters, imidoesters, PFP-esters or hydroxymethyl phosphines.

It will be appreciated that additional peptides are contemplated by the present invention as well as those comprising the amino acid sequences disclosed herein, which may be synthesized (comprising conservative or non-conservative substitutions) in order to "tweak the system" and generate integrin αvβ3 binding peptides with improved characteristics i.e. comprising an enhanced ability to bind integrin αvβ3.

Thus, in other embodiments, the peptide comprises a homolog, a variant, or a functional fragment of the sequences described herein above. In another embodiment, the peptide monomers comprise an amino acid sequence that is about 95%, 96%, 97%, 98% or 99% identical to the sequences described herein above.

Typically, the amino acid substitution is a conservation substitution.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-bacterial properties.

The N and C termini of the peptides of the present invention may be protected by functional groups. Suitable functional groups are described in Green and Wuts, "Protecting Groups in Organic Synthesis", John Wiley and Sons, Chapters 5 and 7, 1991, the teachings of which are incorporated herein by reference.

Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—OO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH$_3$—O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl) (benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the monomers of the present invention. To produce a peptide of the present invention using recombinant technology, a polynucleotide encoding the monomer of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the monomers of the present invention in the host cells.

In addition to being synthesizable in host cells, the peptides of the present invention can also be synthesized using in vitro expression systems. These methods are well known in the art and the components of the system are commercially available.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

According to one embodiment, the peptides of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

It will be appreciated that for therapeutic purposes, the peptides of the present invention may be attached to a therapeutic moiety.

The therapeutic moiety can be, for example, a cytotoxic moiety, a toxic moiety, a cytokine moiety and a second antibody moiety comprising a different specificity to the antibodies of the invention.

Non-limiting examples of therapeutic moieties which can be conjugated to the peptide of the invention are provided in Table 3, hereinbelow.

TABLE 3

| Therapeutic moiety | Amino acid sequence (GenBank Accession No.) | Nucleic acid sequence (GenBank Accession No.) |
|---|---|---|
| Pseudomonas exotoxin | ABU63124 | EU090068 |
| Diphtheria toxin | AAV70486 | AY820132.1 |
| interleukin 2 | CAA00227 | A02159 |
| CD3 | P07766 | X03884 |
| CD16 | NP_000560.5 | NM_000569.6 |
| interleukin 4 | NP_000580.1 | NM_000589.2 |
| HLA-A2 | P01892 | K02883 |
| interleukin 10 | P22301 | M57627 |
| Ricin toxin | EEF27734 | EQ975183 |

It will be appreciated that the peptides of this aspect of the present invention may also be attached to detectable moieties. These peptides can then be used to detect cells which express αvβ3 on their surface. The detection may be effected in vivo or in vitro. The detectable moiety can be a label which is directly visualized (e.g., a fluorescent molecule, a radioactive molecule) or a member of a binding (affinity) pair, which is identifiable via its interaction with an additional member of the binding pair (e.g., antibody-antigen pairs, enzyme-substrate pairs). Table 4, hereinbelow, provides examples of sequences of identifiable moieties.

TABLE 4

| Identifiable Moiety | Amino Acid sequence (GenBank Accession No.) | Nucleic Acid sequence (GenBank Accession No.) |
|---|---|---|
| Green Fluorescent protein | AAL33912 | AF435427 |
| Alkaline phosphatase | AAK73766 | AY042185 |
| Peroxidase | NP_568674 | NM_124071 |
| Histidine tag | AAK09208 | AF329457 |
| Myc tag | AF329457 | AF329457 |
| Biotin lygase tag | NP_561589 | NC_003366 |
| orange fluorescent protein | AAL33917 | AF435432 |
| Beta galactosidase | NM_125776 | NM_125776 |
| Fluorescein isothiocyanate | AAF22695 | AF098239 |
| Streptavidin | S11540 | S11540 |

The functional moiety (the detectable or therapeutic moiety) may be attached or conjugated to the peptides of the invention in various ways, depending on the context, application and purpose.

When the functional moiety is a polypeptide, the conjugate may be produced by recombinant means. For example, the nucleic acid sequence encoding a toxin (e.g., PE38KDEL) or a fluorescent protein [e.g., green fluorescent protein (GFP), red fluorescent protein (RFP) or yellow fluorescent protein (YFP)] may be ligated in-frame with the nucleic acid sequence encoding the peptide of the invention and be expressed in a host cell to produce a recombinant conjugated peptide. Alternatively, the functional moiety may be chemically synthesized by, for example, the stepwise addition of one or more amino acid residues in defined order such as solid phase peptide synthetic techniques.

A functional moiety may also be attached to the antibody of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling of proteins is provided in details in U.S. Pat. Nos. 3,940,475, 4,289,747, and 4,376,110.

Exemplary methods for conjugating peptide moieties (therapeutic or detectable moieties) to the peptide of the invention are described herein below:

SPDP conjugation—A non-limiting example of a method of SPDP conjugation is described in Cumber et al. (1985, Methods of Enzymology 112: 207-224). Briefly, a peptide, such as a detectable or therapeutic moiety (e.g., 1.7 mg/ml) is mixed with a 10-fold excess of SPDP (50 mM in ethanol); the antibody is mixed with a 25-fold excess of SPDP in 20 mM sodium phosphate, 0.10 M NaCl pH 7.2 and each of the reactions is incubated for about 3 hours at room temperature. The reactions are then dialyzed against PBS. The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde conjugation—A non-limiting example of a method of glutaraldehyde conjugation is described in G. T. Hermanson (1996, "Antibody Modification and Conjugation, in Bioconjugate Techniques, Academic Press, San Diego). Briefly, the antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After—the reaction, the excess glutaraldehyde is removed using a G-25 column equilibrated with PBS (10% v/v sample/column volumes).

Carbodiimide conjugation—Conjugation of a peptide with an antibody can be accomplished using a dehydrating agent such as a carbodiimide, e.g., in the presence of 4-dimethyl aminopyridine. Carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond). Likewise, carbodiimide coupling can be used to form analogous covalent bonds between a carbon group of an antibody and an hydroxyl, amino or sulfhydryl group of the peptide [see, J. March, Advanced Organic Chemistry: Reaction's, Mechanism, and Structure, pp. 349-50 & 372-74 (3d ed.), 1985]. For example, the peptide can be conjugated to an antibody via a covalent bond using a carbodiimide, such as dicyclohexylcarbodiimide [B. Neises et al. (1978), Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561)].

It will be appreciated that the peptides of the present invention comprises a myriad of medical uses connected with tissue inflammation e.g., as a healing aid for burn patients and as a dressing to prevent bleeding.

In addition, other medical applications may also benefit from the peptides of the present invention. For example, after abdominal surgery, the intestines and other abdominal organs tend to adhere to one another and to the abdominal wall. It is thought that this adhesion results from post-surgical inflammation. The peptides of the present invention may be delivered directly to the abdominal region.

A soft and flexible device may be implanted between the abdominal wall and internal organs, for example, by attaching it to the abdominal wall, without cutting internal organs, which would lead to infection. The peptides of this aspect of the present invention can be released from the device over a period of months. Such devices includes hydrogels, hyaluronic acid-based membranes, and other materials to solve these problems.

In another embodiment, the peptides of the present invention may be used to coat a metallic stent.

The peptides of the present invention may also be used to coat in vivo sensors and catheters. The peptides may provide a coating for a catheter that is inserted into the area of interest. The peptides of the present invention may also be used for other wounds that are hard to close or that fail to heal properly through normal physiologic mechanisms. For example, diabetics often get skin injuries ("diabetic ulcers"), especially in the lower extremities, which take a long time to heal or fail to heal properly due to poor circulation. The use of the present peptides to these wounds will aid healing and prevent inflammation.

Other implantable medical devices which may be coated with the peptides of the present invention include artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, heart valves, artificial joints, artificial larynxes, otological implants), anastomotic devices, vascular catheter ports, clamps, embolic devices, wound drain tubes, hydrocephalus shunts, pacemakers and implantable defibrillators, and the like.

The peptides of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes.

Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (peptide) effective to prevent, alleviate or ameliorate symptoms of a disorder (e.g., graft disease or atherosclerosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure that levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

ALOS4

Synthetic cyclic peptide (H-cycl (Cys-Ser-Ser-Ala-Gly-Ser-Leu-Phe-Cys)-OH; SEQ ID NO: 4) (Cat #P120301-LG221431, Shanghai Hanhong Scientific Co). For in-vitro experiments, ALOS4 was dissolved in saline and stored at −20° C. at 10 mM stock concentration. Prior to experiments, ALOS4 was thawed and further diluted to working concentrations of 0.3 μM and 30 μM. For in-vivo experiments, ALOS4 was dissolved in saline and stored at −20° C. at 300 mg/kg concentration. Prior to experiments, ALOS4 was thawed and further diluted to working concentrations, of 0.3, 10 and 30 mg/kg.

Cells

HT1080 cells transfected with mCherry reporter under an ISRE (Interferon-Sensitive Response Element) promoter and HCT116 with Luc reporter under ISRE promoter were used. Raw 264.7 (undifferentiated murine macrophages) cell line was also used. The cells were cultured in appropriate media: Dulbecco's Modified Eagle Medium (DMEM) (Cat #41965-039, Gibco) with 4.5 g/l glucose and L-glutamine augmented with 10% FBS (Gibco, Grand Island, NY), 100 U/ml penicillin and 100 μg/ml streptomycin in a humidified atmosphere at 37° C. with 5% $CO_2$.

Animals

Submissive mice are derivates from "Sabra" strain were maintained under a 12 h light/12 h dark cycle with Purina rodent chow (Envigo, Israel) and water provided ad libitum. The animals were housed five per cage. All procedures with animals were performed after review and approval by the Institutional Animal Care and Use Committee of Ariel University.

ISRE Response

HT1080 ISRE mCherry cells were plated in 6-well plates at $2 \times 10^4$ cells/well. The next day DMEM was replaced with DMEM containing 30 μM of ALOS4, 30 μM of RGD, or saline as control and cells continued to grow for 48 hours. Following the 48 hour incubation, 25 μg/well of Polyinosinic:polycytidylic acid (Poly I:C)—a chemical compound structurally similar to double-stranded RNA and acting via Toll Like Receptor-3 molecular pathway activation, was added for an additional 16 h incubation. After this second incubation, cells were subjected to fluorescent imaging followed by washing with 1×PBX, trypsinization and resuspension with 300 μl of 1×PBS. 200 μl of cell suspension were further loaded into 96-well black clear bottom plates. Strength of mCherry fluorescence signal was detected by an ELISA reader with multiple reads per well at $574_{Ex}/610_{Em}$.

HCT116 ISRE Luc cells were plated in 96-well plates at $3 \times 10^3$ cells/well. The next day DMEM was replaced with DMEM containing 0.3 μM of ALOS4 or saline as control with/without PEI—transfection reagent, and cells continued to grow for 48 h. Following the 48 h incubation 1 μg/ml of Poly I:C was added for an additional 16 h incubation. After this second incubation the media was removed, 30 μl of Bright-Glo™ Luciferase Assay System (Promega, Cat #E2610) was added. Plate was read with plate reader on Luminescent parameters.

Cytokines

Blood samples of submissive mice treated with control, as well as 10 and 30 mg/kg of ALOS4 were collected by terminal bleeding from the heart and centrifuged at 14,000 rpm for 20 min. Serum was removed to a new tube and stored at −80° C. for future use. Mouse XL Cytokine Array Kit (Cat #ARYO28, R&D) was used to detect the cytokines in the serum of submissive mice according to the manufacturer's instructions. Serum from treatment groups (saline, 10 and 30 mg/kg ALOS4) was added to each membrane. Streptavidin-HRP and Chemi Reagent Mix were used to detect the antibodies bound to the membrane. The membranes were then exposed (Image Quant LAS4000 mini; GE Healthcare, Milwaukee, WI, USA) and analyzed using ImageQuant TL software (GE Healthcare).

Nitric Oxide Level Assay

Ability of ALOS4 to affect macrophage differentiation to pro- and anti-inflammatory macrophages was evaluated on mouse monocyte macrophages (Raw267.4) using the nitric oxide level assay. Cells were plated at a density of $1 \times 10^5$ cells/ml in 12 well plates for 12 h, followed by treatment with LPS (200 ng/ml) and ALOS4 (0.3 and 30 μM). Nitric oxide production of monocyte differentiation to pro-inflammatory M1 was detected with Griess reaction kit (Cat #G2930, Promega) according to the protocol. The absorbance was read at 540 nm with ELISA plate reader (Tecan infinite M200pro, Switzerland) and nitric oxide concentration was calculated using the Nitrite Standard Reference Curve.

Histology

The adipose tissue of submissive mice treated with 10 and 30 mg/kg of ALOS4 were excised and fixed with 4% formalin overnight at 4° C., followed by dehydration and paraffin embedding (Cat #BN0763, Barnaor). Serial sections of 5 μm thickness were cut and placed on charged glass slides (LE-14035838925, Leica, Germany) and incubated for 1 h at 60° C. At least three slides from each adipose tissue sample with 300 μm distance between sections were collected for histological staining. Prior to Hematoxylin and Eosin (H&E), all sections were subjected to de-paraffinized and hydrated by decreasing concentrations of ethanol in deionized water.

H&E Staining

De-paraffinized and hydrated slides were immersed in Meyer's Hematoxylin solution (Cat #HX68597049, MERCK) for 5 min, washed for 5 min with tap water, and then immersed in Eosin solution (Cat #HX6109259, MERCK) for 2 min, rehydrated and mounted with Entalain.

Imaging

Macrophages were evaluated by a scoring system using light microscopy. A score of 1 is characterized by the absence of crown like structures in framed field, 10-20 crowns characterize the score of 2, a score of 3—20-30 crown like structures, a score of 4—30-40 crowns and a score of 5—abundant crowns (40-50).

Example 1

Anti-Inflammatory Effect of ALOS4

Pretreatment with 0.3 μM of ALOS4 (Cys Ser Ser Ala Gly Ser Leu Phe Cys; SEQ ID NO: 4) for 48 h suppressed the ability of treated HT1080 interferon stimulated response element (ISRE) mCherry cells (FIG. 1A, 1C) as well as HCT116 ISRE Luc cells (FIG. 1B) to induce interferon type I signaling in response to mimics of double stranded RNA (Poly I:C).

Example 2

Sub-chronic treatment (i.v. injections, every second day within 10 days) with 10 and 30 mg/kg of ALOS4 lead to downregulation of total interleukins in blood as compared to the control group (FIG. 2A), as analyzed using the murine cytokine array kit and using the database for Annotation, Visualization and Integrated Discovery (DAVID) v6.8 software. The only exception was IL-1α/IL-1F1—a member of the interleukin 1 cytokine family that includes IL-1α, IL-1β and IL-1 receptor antagonist (IL-1Ra), which did not change. These cytokines act through common receptors and have overlapping roles in the regulation of IL-1 activity [3]. It has been shown that IL-1α is constitutively expressed in many cell types in healthy tissues at a steady state, while its expression can be increased in response to growth factors and pro-inflammatory or stress-associated stimuli [4]. Since the only interleukin that increased was IL-1a, and no other IL-1 members or other interleukins in general had increased expression, it was speculated that upregulation of IL-1α can be explained by a selective response to an unidentified trigger rather than the presence of a generalized inflammatory process. This is supported by the results shown in FIG. 2B which demonstrates a strong tendency toward downregulation of pro-inflammatory markers after treatment with ALOS4.

Adipose tissue is enriched in macrophages and can generate and sustain a robust inflammatory response [5]. Pro-inflammatory processes in adipose tissue can be identified by a histological hallmark called crown-like structures, which represent macrophages surrounding dead or dying adipocytes [6]. Fat pads of sub-chronic treated with 10 and 30 mg/kg of ALOS4 were collected, and H&E staining was performed. Crown-like structures were counted and a decrease in frequency was observed following sub-chronic ALOS4 treatment (FIG. 2C).

Figure 2D:
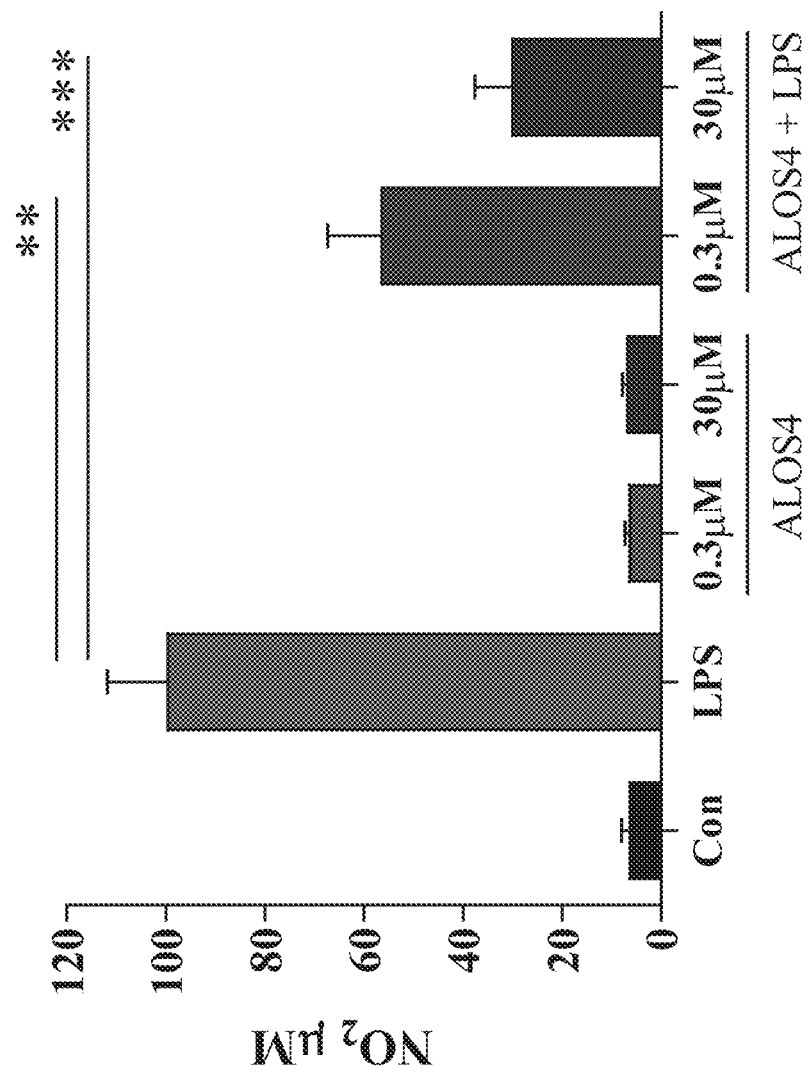

Next, an undifferentiated murine macrophage cell line (Raw267.4) was used to evaluate the effect of ALOS4 on macrophage differentiation under pro-inflammatory stimuli. Raw267.4 cells were treated with lipopolysaccharides (LPS) 200 ng/ml and ALOS4 at a concentration of 0.3 and 30 µM for 24 hours. ALOS4 treatment inhibited differentiation of the macrophages to pro-inflammatory M1 in a dose dependent manner LPS (FIG. 2D).

REFERENCES

1. Nesher, E., et al., *Differential responses to distinct psychotropic agents of selectively bred dominant and submissive animals*. Behav Brain Res, 2013. 236(1): p. 225-35.
2. Feder, Y., et al., *Selective breeding for dominant and submissive behavior in Sabra mice*. J Affect Disord, 2010. 126(1-2): p. 214-22.
3. Huleihel, M., et al., *Over expression of interleukin-1 alpha, interleukin-1beta and interleukin-1 receptor antagonist in testicular tissues from sexually immature mice as compared to adult mice*. Eur Cytokine Netw, 2003. 14(1): p. 27-33.
4. Di Paolo, N. C. and D. M. Shayakhmetov, *Interleukin 1alpha and the inflammatory process*. Nat Immunol, 2016. 17(8): p. 906-13.
5. Ghigliotti, G., et al., *Adipose tissue immune response: novel triggers and consequences for chronic inflammatory conditions*. Inflammation, 2014. 37(4): p. 1337-53.
6. Berger, N. A., *Crown-like Structures in Breast Adipose Tissue from Normal Weight Women: Important Impact*. Cancer Prev Res (Phila), 2017. 10(4): p. 223-225.

What is claimed is:

1. A method of treating type I interferon-associated inflammation due to radiation in a subject in need thereof, the method comprising administering to the subject a therapeutically effective amount of a peptide consisting of cyclic SEQ ID NO: 4, thereby treating the inflammation due to radiation, wherein the N terminus of the peptide is bound to the C terminus of the peptide and wherein the N terminal amino acid and the C terminal amino acids are cysteines.

* * * * *

UNITED STATES PATENT AND TRADEMARK OFFICE
CERTIFICATE OF CORRECTION

| | | |
|---|---|---|
| PATENT NO. | : 12,115,207 B2 | Page 1 of 1 |
| APPLICATION NO. | : 17/068849 | |
| DATED | : October 15, 2024 | |
| INVENTOR(S) | : Andrei Gudkov et al. | |

It is certified that error appears in the above-identified patent and that said Letters Patent is hereby corrected as shown below:

On the Title Page

In item (63) Related U.S. Application Data:
Insert the following:
--Provisional application No. 62/657,035 filed on Apr. 13, 2018--

Signed and Sealed this
Twenty-fourth Day of June, 2025

Coke Morgan Stewart
*Acting Director of the United States Patent and Trademark Office*

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial sequence
<220> FEATURE:
<223> OTHER INFORMATION: ALOS-1 oligopeptide

<400> SEQUENCE: 1

Cys Asn Leu Ser Ser Ser Trp Ile Cys
1               5

<210> SEQ ID NO 2
<211> LENGTH: 9
<212> TYPE: PRT
<213> ORGANISM: Artificial sequence
<220> FEATURE:
<223> OTHER INFORMATION: ALOS-2 oligopeptide

<400> SEQUENCE: 2

Cys Pro Pro Ser Asn His Leu Leu Cys
1               5

<210> SEQ ID NO 3
<211> LENGTH: 9
<212> TYPE: PRT
<213> ORGANISM: Artificial sequence
<220> FEATURE:
<223> OTHER INFORMATION: ALOS-3 oligopeptide

<400> SEQUENCE: 3

Cys Ala Pro Ser Pro Ser Arg Leu Cys
1               5

<210> SEQ ID NO 4
<211> LENGTH: 9
<212> TYPE: PRT
<213> ORGANISM: Artificial sequence
<220> FEATURE:
<223> OTHER INFORMATION: ALOS-3 oligopeptide

<400> SEQUENCE: 4

Cys Ser Ser Ala Gly Ser Leu Phe Cys
1               5

<210> SEQ ID NO 5
```

```
<211> LENGTH: 9
<212> TYPE: PRT
<213> ORGANISM: Artificial sequence
<220> FEATURE:
<223> OTHER INFORMATION: ALOS-5 oligopeptide

<400> SEQUENCE: 5

Cys Pro Leu His Ala Arg Leu Pro Cys
1               5

<210> SEQ ID NO 6
<211> LENGTH: 27
<212> TYPE: DNA
<213> ORGANISM: Artificial sequence
<220> FEATURE:
<223> OTHER INFORMATION: nucleic acids sequence encoding ALOS-1

<400> SEQUENCE: 6
tgtaatcttt cgtcttcatg gatttgc                                         27

<210> SEQ ID NO 7
<211> LENGTH: 27
<212> TYPE: DNA
<213> ORGANISM: Artificial sequence
<220> FEATURE:
<223> OTHER INFORMATION: nucleic acids sequence encoding ALOS-2

<400> SEQUENCE: 7
tgtccgccgt ctaatcatct gttgtgc                                         27

<210> SEQ ID NO 8
<211> LENGTH: 27
<212> TYPE: DNA
<213> ORGANISM: Artificial sequence
<220> FEATURE:
<223> OTHER INFORMATION: nucleic acids sequence encoding ALOS-3

<400> SEQUENCE: 8
tgtgctcctt ctccttctcg gctttgc                                         27

<210> SEQ ID NO 9
<211> LENGTH: 27
<212> TYPE: DNA
<213> ORGANISM: Artificial sequence
<220> FEATURE:
<223> OTHER INFORMATION: nucleic acids sequence encoding ALOS-4

<400> SEQUENCE: 9
tgttcttctg ctggttctct tttttgc                                         27

<210> SEQ ID NO 10
<211> LENGTH: 27
<212> TYPE: DNA
<213> ORGANISM: Artificial sequence
<220> FEATURE:
<223> OTHER INFORMATION: nucleic acids sequence encoding ALOS-5

<400> SEQUENCE: 10
tgtccgcttc atgcgcggct gccttgc                                         27

<210> SEQ ID NO 11
<211> LENGTH: 7
<212> TYPE: PRT
<213> ORGANISM: Artificial sequence
<220> FEATURE:
<223> OTHER INFORMATION: oligopeptide
```

```
<400> SEQUENCE: 11

Asn Leu Ser Ser Ser Trp Ile
1               5

<210> SEQ ID NO 12
<211> LENGTH: 7
<212> TYPE: PRT
<213> ORGANISM: Artificial sequence
<220> FEATURE:
<223> OTHER INFORMATION: oligopeptide

<400> SEQUENCE: 12

Pro Pro Ser Asn His Leu Leu
1               5

<210> SEQ ID NO 13
<211> LENGTH: 7
<212> TYPE: PRT
<213> ORGANISM: Artificial sequence
<220> FEATURE:
<223> OTHER INFORMATION: oligopeptide

<400> SEQUENCE: 13

Ala Pro Ser Pro Ser Arg Leu
1               5

<210> SEQ ID NO 14
<211> LENGTH: 7
<212> TYPE: PRT
<213> ORGANISM: Artificial sequence
<220> FEATURE:
<223> OTHER INFORMATION: oligopeptide

<400> SEQUENCE: 14

Ser Ser Ala Gly Ser Leu Phe
1               5

<210> SEQ ID NO 15
<211> LENGTH: 7
<212> TYPE: PRT
<213> ORGANISM: Artificial sequence
<220> FEATURE:
<223> OTHER INFORMATION: oligopeptide

<400> SEQUENCE: 15

Pro Leu His Ala Arg Leu Pro
1               5

<210> SEQ ID NO 16
<211> LENGTH: 21
<212> TYPE: DNA
<213> ORGANISM: Artificial sequence
<220> FEATURE:
<223> OTHER INFORMATION: oligonucleotide encoding peptide Seq ID 11

<400> SEQUENCE: 16
aatctttcgt cttcatggat t                                            21

<210> SEQ ID NO 17
<211> LENGTH: 21
<212> TYPE: DNA
<213> ORGANISM: Artificial sequence
<220> FEATURE:
<223> OTHER INFORMATION: oligonucleotide encoding peptide Seq ID 12
```

-continued

```
<400> SEQUENCE: 17
ccgccgtcta atcatctgtt g                                              21

<210> SEQ ID NO 18
<211> LENGTH: 21
<212> TYPE: DNA
<213> ORGANISM: Artificial sequence
<220> FEATURE:
<223> OTHER INFORMATION: oligonucleotide encoding peptide Seq ID 13

<400> SEQUENCE: 18
gctccttctc cttctcggct t                                              21

<210> SEQ ID NO 19
<211> LENGTH: 21
<212> TYPE: DNA
<213> ORGANISM: Artificial sequence
<220> FEATURE:
<223> OTHER INFORMATION: oligonucleotide encoding peptide Seq ID 14

<400> SEQUENCE: 19
tcttctgctg gttctctttt t                                              21

<210> SEQ ID NO 20
<211> LENGTH: 21
<212> TYPE: DNA
<213> ORGANISM: Artificial sequence
<220> FEATURE:
<223> OTHER INFORMATION: oligonucleotide encoding peptide Seq ID 15

<400> SEQUENCE: 20
ccgcttcatg cgcggctgcc t                                              21
```